United States Patent [19]

Atsumi et al.

[11] Patent Number: 4,950,660

[45] Date of Patent: Aug. 21, 1990

[54] BETA-LACTAM COMPOUND AND PROCESS FOR PRODUCTION THEREOF

[75] Inventors: Kunio Atsumi; Yuichi Yamamoto; Kenji Sakagami; Ken Nishihata; Shinichi Kondo, all of Yokohama, Japan

[73] Assignee: Meiji Seika Kabushiki Kaisha, Tokyo, Japan

[21] Appl. No.: 240,950

[22] Filed: Sep. 6, 1988

[30] Foreign Application Priority Data

Sep. 7, 1987 [JP] Japan .................................. 62-223260

[51] Int. Cl.$^5$ .................. C07D 501/57; A61K 31/545
[52] U.S. Cl. ..................................... 514/201; 540/221
[58] Field of Search ....................... 540/221; 514/201

[56] References Cited

U.S. PATENT DOCUMENTS

4,385,178  5/1983  Saikawa et al. ..................... 544/26
4,560,750  12/1985  Atsumi et al. ...................... 544/21

FOREIGN PATENT DOCUMENTS

0211526  2/1987  European Pat. Off.

*Primary Examiner*—Mukund J. Shah
*Assistant Examiner*—C. L. Cseh
*Attorney, Agent, or Firm*—Ladas & Parry

[57] ABSTRACT

The present invention relates to a cephem compound of formula (III) shown in the description. The compound is useful as an intermediate for the synthesis of $\beta$-lactam antibiotics of new class and also to a process for producing the same. The cephem compound (III) is produced by reacting a cephem compound of formula (I) with a nitrogen-containing compound of formula (II) under acid-capturing conditions. The process can be performed easily under mild conditions.

6 Claims, No Drawings

BETA-LACTAM COMPOUND AND PROCESS FOR PRODUCTION THEREOF

BACKGROUND OF THE INVENTION

1. Field of the Invention

The present invention relates to an intermediate useful for the synthesis of β-lactam antibacterial agents of new-class and also to a process for producing the same.

2. Prior Art and Problems

It has recently been reported that a cephalosporin derivative having a formylamino group at the 7α position of the nucleus is found in a culture medium of *Flavobacterium sp.* SC12,154, which is one species of bacteria, and exhibits an antibacterial action. (The Journal of Antibiotics, Vol. 37, No. 7, pp. 773–780, 1984)

Also, according to recent disclosures, β-lactam antibiotics of new-class having a formylamino group on the carbon atom adjacent to the carbonyl group of the β-lactam ring have been chemically synthesized, and exhibit an antibacterial action for a large variety of gram-negative bacteria and gram-positive bacteria. (Japanese Patent Laid-open No. 38288/1983 and The Journal of Antibioitics, Vol. 39, p. 1788, 1986)

According to the literature cited above, β-lactam antibiotics of new-class having a formylamino group are prepared by introducing an amino group onto the carbon atom adjacent to the carbonyl group of the β-lactam ring and then formylating the amino group by a conventional method.

Therefore, in the production of these β-lactam antibiotics of new-class having a formylamino group, a 7α-aminocephalosporin derivative represented by formula (A) below (for which the cephem nucleus is taken as an example) is an important intermediate, and the process for its production constitutes a problem.

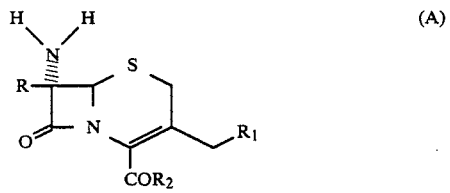

wherein $R_1$ denotes a hydrogen atom or a group-A-B (where A denotes an oxygen atom or sulfur atom and B denotes (a) an acyl group, (b) a substituted or unsubstituted heterocyclic group containing as a ring member at least one kind of hetero-atom selected from the group consisting of oxygen atom, nitrogen atom, and sulfur atom, or (c) a substituted or unsubstituted carbamoyl group); $R_2$ denotes a protective group of the hydroxyl group or carboxyl group; and R denotes an acylamino group or protected amino group.

There have already been disclosed the following processes for the production of the intermediate (A).

(i) Processes disclosed in U.S. Pat. No. 3,962,214 and U.K. Pat. No. 1,348,984.

According to one of these processes, the intermediate is prepared by reacting 7β-acylamino-7α-alkyl- (or aryl- or benzyl-) thio-cephalosporin with anhydrous ammonia, an ammonium salt, or an amine in the presence of a heavy metal ion such as mercury, silver, thallium, lead, and copper ions.

According to another process, the intermediate is prepared by reacting 7β-acylamino-7α-alkyl- (or aryl- or benzyl-) thio-cephalosporin with chlorine or bromine at a low temperature (produced by dry ice), thereby changing the 7α-side chain into a halosulfonium halide, and reacting the resulting compound with anhydrous ammonia, an ammonium salt, or an amine.

According to yet another process, the intermediate is prepared by oxidizing the 7α-side chain of 7β-acylamino-7α-alkyl-(or aryl- or benzyl-) thio-cephalosporin into sulfoxide and reacting the resulting compound with anhydrous ammonia, an ammonium salt, or an amine.

The 7β-acrylamino-7α-alkyl- (or alkyl- or benzyl-) thio-cephalosporin used as the starting material in the above-mentioned processes is produced from a 7-aminocephalosporin derivative by the steps of Schiff base formation, sulfenylation, cleavage of Schiff base, and acylation.

(ii) Process disclosed in Japanese Patent Laid-open No. 118789/1976.

According to this process, the intermediate is produced from 7β-acylamino-7α-alkyl- (or aryl- or benzyl-) seleno-cephalosporin as the starting material by the same steps as in process (i) mentioned above.

The above-mentioned processes, however, would suffer from several disadvantages. For example, they use as the starting material a 7-substituted thio- (or seleno-) cephem compound which is synthesized by sulfenylation or selenylation which is performed under comparatively severe conditions; they employ a heavy metal salt or use a low temperature (about −80° C.); and they need comparatively long steps and give the desired product in rather poor yields. Under these circumstances, there is a demand for a more convenient and commercially satisfactory process for introducing an amino group into the 7α position of the cephem ring.

SUMMARY OF THE INVENTION

Means to Solve the Problems/Summary of the Invention

The present inventors carried out a series of researches in search of a new, highly selective, highly efficient aminating reaction which can be performed under mild conditions by simple operations. As the result, they found a new process for producing a compound represented by the formula (III) below which is a derivative of the compound represented by formula (A) given earlier

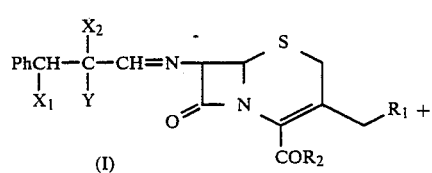

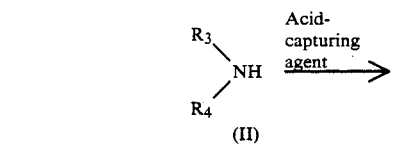

-continued

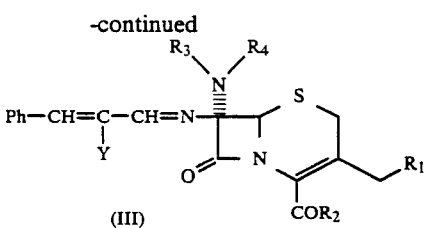

(III)

wherein $R_1$ denotes a hydrogen atom or a group-A-B (where A denotes an oxygen atom or sulfur atom and B denotes (a) an acyl group, (b) a substituted or unsubstituted heterocyclic group containing as a ring member at least one kind of hetero atom selected from the group consisting of oxygen atom, nitrogen atom, and sulfur atom, or (c) a substituted or unsubstituted carbamoyl group); $R_2$ denotes a protective group for the hydroxyl group or carboxyl group; $R_3$ and $R_4$ are the same or different, each representing a hydrogen atom or a lower alkyl group having 1 to 4 carbon atoms, or $R_3$ denotes a hydrogen atom and $R_4$ denotes a lower alkoxyl group having 1 to 4 carbon atoms; $X_1$ and $X_2$ denote the same or different halogen atoms; and Y denotes a chlorine atom or bromine atom.

Accordingly, the present invention relates to a new compound, which is a cephem compound represented by formula (III).

The present invention also relates to a process for producing this new compound, said process comprising reacting a cephem compound represented by formula (I) with a nitrogen-containing compound or an acid salt thereof represented by formula (II) under the acid-capturing conditions. Formulas (I) to (III) are as shown above.

Advantages of the Invention

The new compound (III) of the present invention can be easily and advantageously synthesized without the difficulties encountered in the production of the above-mentioned known compound (A).

The compound (III), like the known compound (A), is an intermediate useful for the synthesis of β-lactam antibiotics of new-class having the above-mentioned formylamino group. For more detail about the advantages of the present invention, refer to the paragraph entitled "Evaluation and Development of the Invention."

DETAILED DESCRIPTION OF THE INVENTION

Cephem compound (III)

The cephem compound (III) according to the present invention is one which is represented by the above-mentioned formula (III).

The cephem compound (III) is typified mainly by those compounds in which $R_1$ is a group-A-B, preferably those compounds in which A in the group-A-B is a sulfur atom.

The acyl group (a), which is an embodiment of B in the case where $R_1$ is a group-A-B, includes acyl groups having up to about 4 carbon atoms, which may optionally have a substituting group, such as acetyl group and acetoacetyl group. The heterocyclic group (b), which is another embodiment of B, may optionally have a substituting group such as a lower alkyl group, aminoalkyl group, or sulfoalkyl group. Examples of the heterocyclic group include 1H-tetrazol-5-yl group, 1H-1-methyltetrazol-5-yl group, 1-carboxymethyl-1H-tetrazol-5-yl group, 2-carboxymethyl-1H-triazol-5-yl group, 1-sulfoethyl-1H-tetrazol-5-yl group, 2-carboxymethyl-1-methyl-1H-triazol-5-yl group, 4-methyl-5-oxo-6-hydroxy-4,5-dihydro-1,2,4-triazin-3-yl group, pyridinium-methyl group, triazolyl group, and thiadiazolyl group. Examples of the substituted carbamoyl group (c) include monosubstituted and disubstituted carbamoyl groups, substituent being, for example, an alkyl group (typically a lower alkyl group).

$R_2$ is a protective group for the hydroxyl group or carboxyl group. Examples of the protective group for the carboxyl group are those commonly used in the field of penicillins and cephalosporins, and include diphenylmethoxy group, tert-butoxy group, p-nitrobenzyloxy group, 2,2,2-trichloroethoxy group, and methoxymethoxy group.

Y may preferably be the same halogen as $X_1$ and $X_2$, particularly, chlorine, from the standpoint of the manufacturing process.

Typical examples of the cephem compounds represented by formula (III) in the present invention include the following.

(i) 7β-(2-chloro(3-phenylprop-2-en-1-ylideneamino))-7β-amino-3-(1-methyl-1H-tetrazol-5-yl)thiomethyl-3-cephem-4-carboxylic diphenylmethyl ester.

(ii) 7β-(2-chloro(3-phenylprop-2-en-1-ylideneamino))-7α-amino-3-(2-methyl-1,3,4-thiadiazol-5-yl)thiomethyl-3-cephem-4-carboxylic diphenylmethyl ester.

(iii) 7β-(2-chloro(3-phenylprop-2-en-1-ylideneamino))-7α-methoxyamino-3-(1-methyl-1H-tetrazol-5-yl)thiomethyl-3-cephem-4-carboxylic diphenylmethyl ester.

(iv) 7β-(2-chloro(3-phenylprop-2-en-1-ylideneamino))-7α-methylamino-3-(1-methyl-1H-tetrazol-5-yl)thiomethyl-3-cephem-4-carboxylic diphenylmethyl ester.

(v) 7β-(2-chloro(3-phenylprop-2-en-1-ylideneamino))-7α-dimethylamino-3-(1-methyl-1H-tetrazol-5-yl)thiomethyl-3-cephem-4-carboxylic diphenylmethyl ester.

For reference, the examples of the substituent groups in formula (III) are shown below.

| Compound | Y | $R_1$* | $R_2$ | $R_3$ | $R_4$ |
|---|---|---|---|---|---|
| i | Cl | a | —OCHPh$_2$ | H | H |
| ii | Cl | b | —OCHPh$_2$ | H | H |
| iii | Cl | a | —OCHPh$_2$ | H | —OCH$_3$ |
| iv | Cl | a | —OCHPh$_2$ | H | —CH$_3$ |
| v | Cl | a | —OCHPh$_2$ | —CH$_3$ | —CH$_3$ |

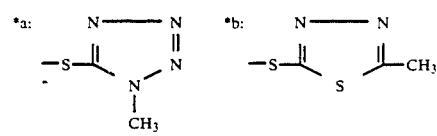

Synthesis of Cephem Compound (III)

The cephem compound (III) of the present invention may be synthesized by any suitable process available.

One of the processes comprises aminating the cephem compound of formula (I) above of the present invention with a nitrogen-containing compound of formula (II).

According to the process of the present invention, a cephem compound of formula (I) is reacted with a nitrogen-containing compound represented by formula (II)

(where $R_3$ and $R_4$ are defined as above) or an acid salt thereof under the acid-capturing conditions.

Examples of the nitrogen-containing compound (II) include ammonia, lower alkyl amines such as methylamine, di(lower alkyl) amines such as dimethylamine, and lower alkoxy amines such as methoxyamine.

The cephem compound of formula (I) corresponds to a Schiff base composed of a 7-aminocephem compound of formula (IV) below

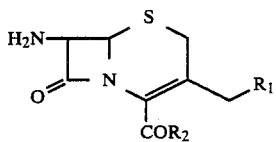

(where $R_1$ and $R_2$ are defined as above) and a 3-phenyl-2,2,3-trihalo-1-propanal represented by formula (V) below

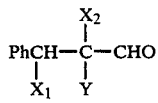

(where $X_1$, $X_2$, and $Y$ are defined as above).

The resulting compound is a new 7α-aminocephem compound corresponding to the nitrogen-containing compound used, and is the compound of formula (III) which is the desired compound in the present invention.

The reaction to convert compound (I) into compound (III) is usually carried out in an organic solvent at room temperature or below. However, the reaction may preferably be performed with ice cooling. The reaction is performed under the acid-capturing conditions. The acid-capturing agent for this purpose includes basic inorganic salts such as borax, potassium carbonate, and sodium carbonate. The nitrogen-containing compound (II) or a borate or carbonate thereof also functions as the acid-capturing agent. Therefore, if the nitrogen-containing compound (II) is used in excess, the desired reaction proceeds smoothly even though an acid-capturing agent is not intentionally added. In the present invention, both cases are regarded as reactions "under the acid-capturing conditions." The halogens $X_1$ and $X_2$ in compound (I) which afford hydrogen halides to be captured by the acid-capturing agent should typically be chlorine.

The compound of formula (I) or the Schiff base (I) may be prepared from 7-aminocephem compound (IV) and 3-phenyl-2,2,3-trihalo-1-propanal (V) by a known process (as disclosed in Japanese Patent Laid-open No. 169488/1982) when preparation by chemical synthesis is desired.

Evaluation and Development of the Present Invention

According to the present invention, the compound of formula (I) is aminated with the compound of formula (II). This reaction is new and different from the conventional one. It eliminates 2 moles of hydrogen halide from 1 mole of the compound (I) as the starting material, and adds 1 mole of the nitrogen-containing compound (II) to the compound (I), eventually yielding the compound (III) which is a stable reaction product. In other words, the reaction is an oxidative aminating reaction to convert the hydrogen atom at the 7α position of the cephem ring into an amino group in a single step. Therefore, it proceeds in an entirely different manner from that employed in the conventional process. The reaction in the present invention is, in actual, the elimination of hydrogen halide and the nucleophilic addition of the nitrogen-containing compound (II), but it may be regarded, in form, as an oxidative aminating reaction.

The reaction in the present invention has several advantages over the conventional aminating reaction. That is, it dispenses with a 7-substituted thio- (or seleno-) cephem compound as the starting material which undergoes comparatively severe reactions such as sulfenylation (or selenylation) which needs many reaction steps. It proceeds to bring about amination (or substitution amination) at the 7α position, under mild reaction conditions without the aid of a heavy metal-containing reagent. In addition, it facilitates collection of the reaction product and affords the desired product efficiently.

Among the compounds (III) synthesized by the process of the present invention, the one in which at least either of $R_3$ or $R_4$ is a hydrogen atom, is an intermediate useful for the synthesis of 7α-formylaminocephalosporin derivatives which are β-lactam antibiotics of new class. The usefulness is derived from the following characteristic properties. One of the compounds (III) in which at least either of $R_3$ or $R_4$ is a hydrogen atom, as represented by the formula (III') below, can be easily converted by formylation into the 7α-formylamino (or formyl substituted-amino) form (VI) by a conventional method wherein a formic acid-acetic anhydride mixture is used. In addition, the compound (IV) is as Schiff base, which facilitates the elimination of the aldehyde moiety as mentioned in the following.

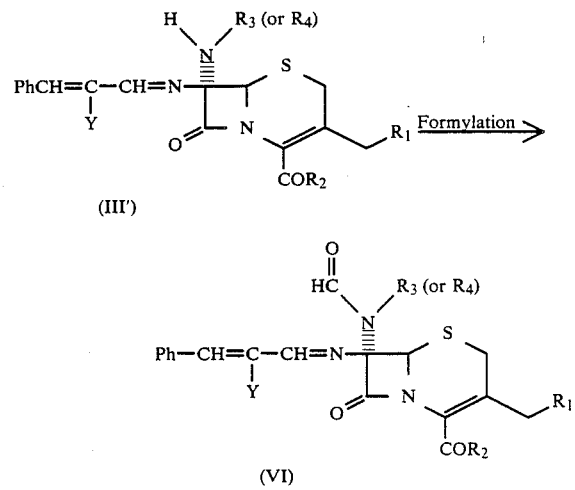

(where $R_1$, $R_2$, $R_3$, $R_4$, and $Y$ are defined as above.)

That is, when the compound (VI) is treated in the usual way with a substituted hydrazine derivative, especially Girard reagent (as described in Reagents for Organic Synthesis, p. 410, by Fieser and Fieser, 1967) which captures an aldehyde or ketone, the aldehyde moiety (or the 3-phenyl-2-halopropenal moiety) of the compound (VI), which is the Schiff base, is readily eliminated to give a 7β-amino-7α-formylamino- (or formyl-substituted-amino-) cephem compound (VII).

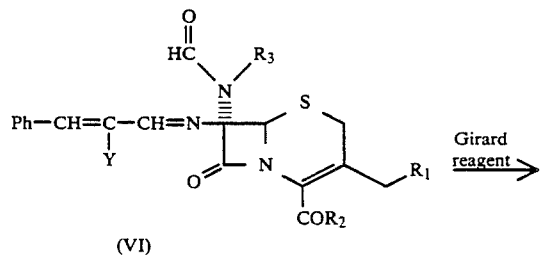

(VI)

(VII)

The thus formed compound (VII) is readily acylated into 7β-acylamino-7α-formylamino- (or formyl-substituted-amino-) cephem compound (VIII), when it is reacted with a carboxylic acid in active form.

(VII) → RCOZ →

(VIII)

(where $R_1$, $R_2$, $R_3$, and $R_4$ are defined as above, and RCOZ denotes a carboxylic acid RCOOH in active form such as acid halide, mixed acid anhydride, active ester, and active amide.)

The compound (VIII) can be converted into cephalosporin preparations of new class having an antibacterial action, as disclosed in, for example, The Journal of Antibiotics, Vol. 39, p. 1788, 1986, and Japanese Patent Laid-open No. 38288/1983, when the acyl side chain is chemically modified or, if necessary, the protective group is removed according to any known method that suits the intended object.

For instance, the compound (VIII-1), which is a particular compound of the compound (VIII) in which $R_1$ is 1-methyl-1H-tetrazol-5-yl thiomethyl group, $R_2$ is diphenylmethoxy group, and R is bromoacetyl group, can be readily converted, by the process shown below, into 7β-[[2(R)-2-amino-2-carboxyethylthio]acetamido]-7α-formylamino-3[[(1-methyl-1H-tetrazol-5-yl)thio]-methyl]-3-cephem-4-carboxylic acid (IX). The compound (IX) is a cephem ring 7α-formylamino analog of Cefminox (MT141) (See Japanese Patent Laid-open No. 83791/1980), which is a useful cephamycin antibiotic, and it is also a new antibacterial agent per se.

(VIII-1)

(IX)

The compound (IX) was examined for minimum inhibitory concentration by the agar dilution method. The results are shown in the following table.

| Bacteria tested | Minimum inhibitory concentration (μg/ml) |
|---|---|
| *Escherichia coli* NIHJ JC-2 | 1.56 |
| *Escherichia coli* No. 29 | 1.56 |
| *Escherichia coli* 255 | 3.13 |
| *Proteus rettgeri* GN624 | 1.56 |
| *Citorobacter freundii* GN346 | 1.56 |
| *Enterobactor cloacae* GN7471 | 1.56 |

| Bacteria tested | Minimum inhibitory concentration (μg/ml) |
|---|---|
| *Serratia marcescens* GN10857 | 3.13 |

EXPERIMENT EXAMPLES

The following examples and referential examples are presented not to limit but to explain the present invention in more detail.

EXAMPLE 1

7β-(2-chloro(3-phenylprop-2-en-1-ylideneamino))-7α-amino-3-(1-methyl-1H-tetrazol-5-yl)thiomethyl-3-cephem-4-carboxylic diphenyl ester

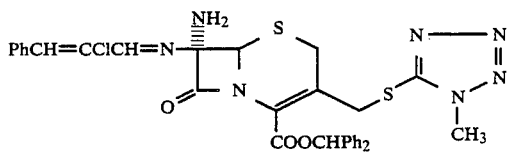

7β-(2,2,3-trichloro(3-phenyl-1-propylideneamino))-3-(1-methyl-1H-tetrazol-5-yl)thiomethyl-3-cephem-4-carboxylic diphenylmethyl ester (7.14 g, 10 mmol) was dissolved in a mixed solvent of dimethyl sulfoxide (75 ml) and ethyl acetate (75 ml). To the solution, with ice cooling, were added ammonium borate tetrahydrate (10.1 g, 40 mmol) and methanol (75 ml), followed by stirring for 2 hours. To the reaction liquid was added iced water (150 ml), and the solution was extracted with ethyl acetate (75 ml, twice). The extract was washed with water, dried with anhydrous magnesium sulfate, and concentrated under reduced pressure. For isolation and purification, the concentrate was subjected to silica gel flush column chromatography (eluted with benzene:ethyl acetate=5:1). A quantity of 4.6 g (70%) of the title compound in the form of foam was obtained.

NMR δppm (CDCl₃): 2.1 (2H, broad s), 3.60 (1H, d, J=18 Hz), 3.64 (1H, d, J=18 Hz), 3.80 (3H, s), 4.22 (1H, d, J=13 Hz), 4.35 (1H, d, 13 Hz), 4.92 (1H, s), 6.97 (1H, s), 7.1–7.6 (14H, m), 7.7–7.9 (2H, m), 8.39 (1H, s).

EXAMPLE 2

7β-(2-chloro(3-phenylprop-2-en-1-ylideneamino))-7α-amino-3-(2-methyl-1,3,4-thiadiazol-5-yl)thiomethyl-3-cephem-4-carboxylic diphenyl ester

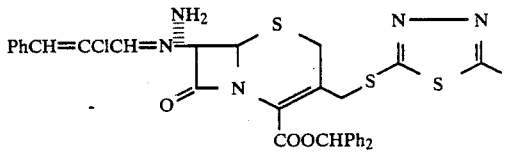

7β-(2,2,3-trichloro(3-phenyl-1-propylideneamino))-3-(2-methyl-1,3,4-thiadiazol-5-yl)thiomethyl-3-cephem-4-carboxylic diphenylmethyl ester (3.70 g, 5 mmol) was dissolved in a mixed solvent of dimethyl sulfoxide (40 ml) and ethyl acetate (40 ml). To the solution, with ice cooling, were added ammonium borate tetrahydrate (5.05 g, 20 mmol) and methanol (40 ml), followed by stirring for 2 hours. To the reaction liquid was added ice water (80 ml), and the solution was extracted with ethyl acetate (40 ml, twice). The extract was washed with water, dried with anhydrous magnesium sulfate, and concentrated under reduced pressure. For isolation and purification, the concentrate was subjected to silica gel flush column chromatography (eluted with benzene:ethyl acetate=5:1). A quantity of 2.2 g (65%) of the title compound in the form of foam was obtained.

NMR δ ppm (CDCl₃): 2.3 (2H, broad s), 2.63 (3H, s), 3.53 (1H, d, J=17 Hz), 3.63 (1H, d, J=17 Hz), 4.14 (1H, d, 13 Hz), 4.24 (1H, d, 13 Hz), 4.89 (1H, s), 6.97 (1H, s), 7.2–7.5 (14H, m), 7.7–7.9 (2H, m), 8.34 (1H, s).

EXAMPLE 3

7β-(2-chloro(3-phenylprop-2-en-1-ylideneamino))-7α-methoxylamino-3-(1-methyl-1H-tetrazol-5-yl)thiomethyl-3-cephem-4-carboxylic diphenylmethyl ester

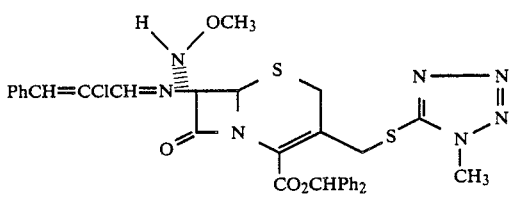

Methanol (12 ml) was added to methoxylamine hydrochloride (0.668 g, 8 mmol) and borax (3.05 g, 8 mmol), followed by stirring with ice cooling for 30 minutes. The resulting suspension was dropwise (over 5 minutes), with ice cooling, to a dimethylformamide solution (15 ml) of 7β-(2,2,3-trichloro(3-phenyl-1-propylideneamino))-3-(1-methyl-1H-tetrazol-5-yl)thiomethyl-3-cephem-4-carboxylic diphenylmethyl ester (1.428 g, 2 mmol). The solution was stirred for 10 minutes at the same temperature. To the reaction liquid was added iced water (50 ml), and the solution was extracted with ethyl acetate (30 ml, twice). The extract was washed with water, dried with anhydrous magnesium sulfate, and concentrated under reduced pressure. For isolation and purification, the concentrate was subjected to silica gel flush column chromatography (eluted with benzene: ethyl acetate=5:1). A quantity of 1.087 g (79%) of the title compound was obtained.

NMR δ ppm (CDCl₃): 3.53 (3H, s), 3.60 (1H, d, J=18 Hz), 3.71 (1H, d, J=18 Hz), 3.81 (3H, s), 4.25 (1H, d, J=13Hz), 4.38 (1H, d, J=13 Hz), 5.21 (1H, s), 6.10 (1H, broad s), 6.92 (1H, s), 7.1–7.7 (14H, m), 7.7–8.0 (2H, m), 8.51 (1H, s).

EXAMPLE 4

7β-(2-chloro(3-phenylprop-2-en-1-ylideneamino))-7α-methylamino-3-(1-methyl-1H-tetrazol-5-yl)thiomethyl-3-cephem-4-carboxylic diphenylmethyl ester

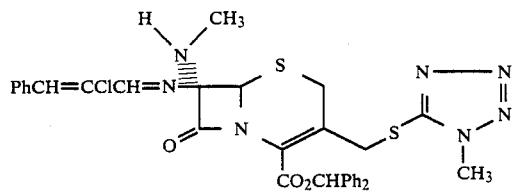

The same procedure as in Example 3 was repeated except that the methoxylamine hydrochloride was replaced by methylamine hydrochloride. The title compound was obtained in a yield of 75%.

NMR δ ppm (CDCl₃): 2.0 (1H, broad s), 2.54 (3H, s), 3.62 (1H, d, J=18 Hz), 3.66 (1H, d, J=18 Hz), 3.81 (3H, s), 4.20 (1H, d, J=13 Hz), 4.35 (1H, d, J=13 Hz), 5.03 (1H, s), 6.93 (1H, s), 7.1–7.7 (14H, m), 7.7–8.0 (2H, m), 8.41 (1H, s).

EXAMPLE 5

7β-(2-chloro(3-phenylprop-2-en-1-ylideneamino))-7α-dimethylamino-3-(1-methyl-1H-tetrazol-5-yl)thiomethyl-3-cephem-4-carboxylic diphenylmethyl ester

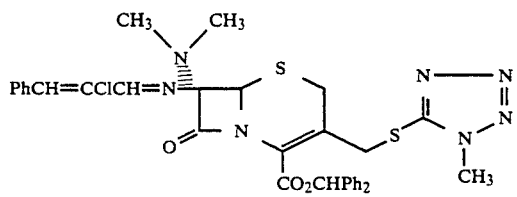

The same procedure as in Example 3 was repeated except that the methoxylamine hydrochloride was replaced by dimethylamine hydrochloride. The title compound was obtained in a yield of 75%.

NMR δ ppm (CDCl₃): 2.46 (6H, s), 3.60 (1H, d, J=18 Hz), 3.71 (1H, d, J=18 Hz), 3.79 (3H, s), 4.22 (1H, d, J=13 Hz), 4.35 (1H, d, J=13 Hz), 5.08 (1H, s), 6.93 (1H, s), 7.1–7.7 (14H, m), 7.7–8.0 (2H, m), 8.43 (1H, s).

REFERENTIAL EXAMPLE 1

7β-(2-chloro(3-phenylprop-2-en-1-ylideneamino))-7α-formamino-3-(1H-tetrazol-5-yl)thiomethyl-3-cephem-4-carboxylic diphenylmethyl ester

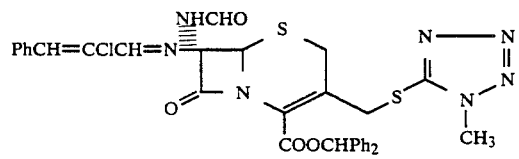

7β-(2-chloro(3-phenylprop-2-en-1-ylideneamino))-7α-amino-3-(1-methyl-1H-tetrazol-5-yl)thiomethyl-3-cephem-4-carboxylic diphenylmethyl ester (3.29 g, 5 mmol) was dissolved in ethyl acetate (75 ml). To the solution, with ice cooling, were added a mixture of acetic anhydride (0.51 g, 5 mmol) and formic acid (0.23 g, 5 mmol) which had been heated at 50° C. for 30 minutes, and pyridine (0.4 g, 5 mmol), followed by stirring for 1 hour. To the reaction liquid was added iced water (50 ml), and the solution was extracted with ethyl acetate (40 ml). The extract was washed with water, dried with anhydrous magnesium sulfate, and concentrated under reduced pressure. For isolation and purification, the concentrate was subjected to silica gel flush column chromatography (eluted with benzene: ethyl acetate=5:1). A quantity of 2.8 g (82%) of the title compound was obtained.

NMR δ ppm (CDCl₃): 3.61 (2H, s), 3.78 (3H, s), 4.23 (1H, d, J=13 Hz), 4.31 (1H, d, J=13 Hz), 5.37 (1H, s), 6.98 (1H, s), 7.1–7.6 (14H, m), 7.7–7.9 (2H, m), 8.19 (1H, s), 8.28 (1H, s).

REFERENTIAL EXAMPLE 2

7β-(2-chloro(3-phenylprop-2-en-1-ylideneamino))-7α-formamino-3-(2-methyl-1,3,4-thiadiazol-5-yl)thiomethyl-3-cephem-4-carboxylic diphenylmethyl ester

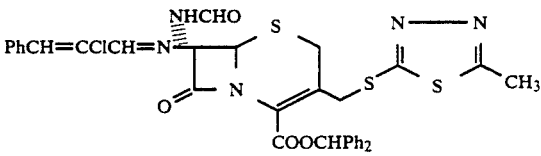

7β-(2-chloro(3-phenylprop-2-en-1-ylideneamino))-7α-amino-3-(2-methyl-1,3,4-thiadiazol-5-yl)thiomethyl-3-cephem-4-carboxylic diphenylmethyl ester (1.35 g, 2 mmol) was dissolved in ethyl acetate (20 ml). To the solution, with ice cooling, were added a mixture of acetic anhydride (0.204 g, 2 mmol) and formic acid (0.092 g, 2 mmol) which had been heated at 50° C. for 30 minutes, and pyridine (0.16 g, 2 mmol), followed by stirring for 1 hour. To the reaction liquid was added iced water (20 ml), and the solution was extracted with ethyl acetate (20 ml). The extract was washed with water, dried with anhydrous magnesium sulfate, and concentrated under reduced pressure. For isolation and purification, the concentrate was subjected to silica gel flush column chromatography (eluted with benzene: ethyl acetate=5:1). A quantity of 1.12 g (80%) of the title compound was obtained.

NMR δ ppm (CDCl₃): 2.64 (3H, s), 3.57 (2H, s), 4.20 (1H, d, J=13 Hz), 4.43 (1H, d, J=13 Hz), 5.37 (1H, s), 6.97 (2H, s), 7.1–7.6 (14H, m), 7.65–7.85 (2H, m), 8.14 (1H, s), 8.26 (1H, s).

REFERENTIAL EXAMPLE 3

7β-amino-7α-formamino-3-(1-methyl-1H-tetrazol-5-yl)thiomethyl-3-cephem-4-carboxylic diphenylmethyl ester

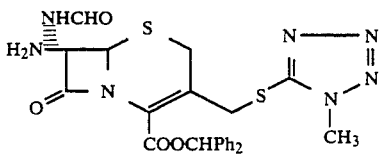

7β-(2-chloro(3-phenylprop-2-en-1-ylideneamino))-7α-formamino-3-(1-methyl-1H-tetrazol-5-yl)thiomethyl-3-cephem-4-carboxylic diphenylmethyl ester (2.06 g, 3 mmol) was dissolved in ethyl acetate (15 ml). To the solution, kept at −40° C. or below, were added (over 10 minutes) a methanol solution (10 ml) of Girard reagent T (1 g, 6 mmol) and p-toluenesulfonic acid monohydrate (1.14 g). The solution was stirred for 1 hour at the same temperature. The reaction liquid was added to a mixture of 6% aqueous solution of sodium bicarbonate (100 ml) and ethyl acetate (30 ml). The resulting solution was separated into two layers. The organic layer was washed with water, dried with anhydrous magnesium sulfate, and concentrated under reduced pressure. For isolation and purification, the concentrate was subjected to silica gel flush column chromatography (eluted with benzene: ethyl acetate=5:1). A quantity of 1.45 g (90%) of the title compound was obtained.

NMR δ ppm (CDCl₃): 2.5 (2H, broad s), 3.60 (2H, s), 3.82 (3H, s), 4.30 (1H, d, J=17 Hz), 4.41 (1H, s, J=17

Hz), 5.14 (1H, s), 6.75 (1H, s), 6.97 (1H, s), 7.2–7.6 (10H, m), 8.14 (1H, s).

REFERENTIAL EXAMPLE 4

7β-bromacetylamino-7α-formamino-3(1-methyl-1H-tetrazol-5-yl)thiomethyl-3-cephem-4-carboxylic diphenylmethyl ester

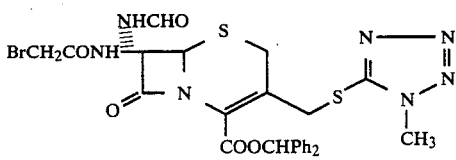

7β-amino-7α-formamino-3-(1-methyl-1H-tetrazol-5-yl)thiomethyl-3-cephem-4-carboxylic diphenylmethyl ester (1.75 g, 2 mmol) was dissolved in ethyl acetate (20 ml). To the solution, with ice cooling, were added dimethylaniline (0.24 g, 2 mmol) and bromoacetyl bromide (0.4 g, 2 mmol). The solution was stirred for 10 minutes at the same temperature. The reaction liquied was extracted with iced water (10 ml) and ethyl acetate (20 ml). The organic layer was washed with 0.1N hydrochloric acid (10 ml, 3 times) and with water (10 ml), dried with anhydrous magnesium sulfate, and concentrated under reduced pressure. For isolation and purification, the concentrate was subjected to silica gel flush column chromatography (eluted with benzene: ethyl acetate=5:1). A quantity of 1.18 g (90%) of the title compound was obtained.

NMR δ ppm (CDCl$_3$): 3.50 (1H, d, J=18 Hz), 3.52 (1H, d, J=18 Hz), 3.82 (3H, s), 3.87 (2H, s), 4.30 (1H, d, J=14 Hz), 4.46 (1H, d, J=14 Hz), 5.20 (1H, s), 6.90 (1H, s), 7.10–7.50 (10H, m), 8.11 (1H, s), 8.23 (1H, s), 8.33 (1H, s).

REFERENTIAL EXAMPLE 5

Sodium 7β-(2D-amino-carboxyethylthhioacetamino)-7α-formamino-3-(1-methyl-1H-tetrazol-5-yl)thiomethyl-3-cephem-4-carboxylate

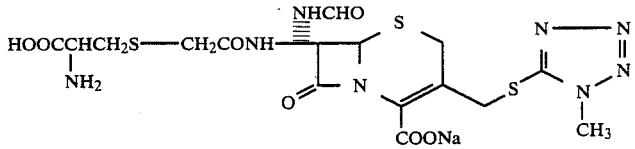

(1) 7β-bromacetylamino-7α-formamino-3-(1-methyl-1H-tetrazol-5-yl)-thiomethyl-3-cephem-4-carboxylic diphenyl ester (0.66 g, 1 mmol) was dissolved in methylene choloride (5 ml). To the solution, with ice cooling, were added anisole (1.08 g, 10 mmol) and trifluoroacetic acid (0.57 g, 5 mmol), followed by stirring for 15 minutes. The reaction liquid was added to isopropyl ether (50 ml), and the solids which had separated out were filtered off, followed by washing with a small amount of isopropyl ether and drying.

Thus there was obtained 0.44 g of 7β-bromacetylamino-7α-formamino-3-(1-methyl-1H-tetrazol-5-yl)thiomethyl-3-cephem-4-carboxylic acid.

(2) In water (5 ml) was suspended 7β-bromacetylamino-7α-formamino-3-(1-methyl-1H-tetrazol-5-yl)thiomethyl-3-cephem-4-carboxylic acid. To the suspension, with ice cooling, was added a saturated solution of sodium bicarbonate to effect dissolution at pH 7.0. To the solution was added D-cysteine (100 mg,) followed by stirring for 1 hour, during which the solution was kept at pH 6.8 with a saturated solution of sodium bicarbonate. The reaction liquid was subjected to colunm chromatography "Diaion HP-20" (eluted with water). The fraction containing the title compound was freeze-dried. Thus a quantity of 0.22 g (39.7%) of the desired compound was obtained.

NMR δ ppm (D$_2$O):3.05 (1H, dd, J=4 Hz, J=2 Hz), 3.12 (1H, dd, J=4 Hz, J=1.2 Hz), 3.43 (1H, d, J=4 Hz), 3.44 (1H, d, J=4 Hz), 3.45 (1H, d, J=4 Hz), 3.74 (1H, d, J=4 Hz), 3.77 (1H, dd, J=2 Hz, J=1.2 Hz), 4.02 (1H, d, J=4.4 Hz), 4.04 (3H, s), 4.25 (1H, d, J=4.4 Hz), 5.31 (1H, s), 8.16 (1H, s).

REFERENTIAL EXAMPLE 6

7β-(2-chloro(3-phenylprop-2-en-1-ylideneamino))-7α-(formylmethoxylamino-3-(1-methyl-1H-tetrazol-5-yl)thiomethyl-3-cephem-4-carboxylic diphenylmethyl ester

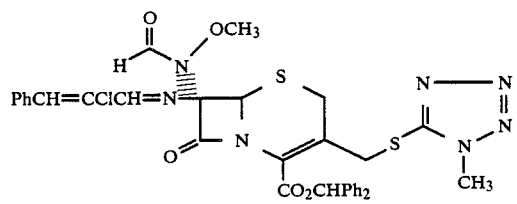

7β-(2-chloro(3-phenylprop-2-en-1-ylideneamino))-7α-methoxylamino-3-(1-methyl-1H-tetrazol-5-yl)-thiomethyl-3-cephem-4-carboxylic diphenylmethyl ester (0.350 g, 1 mmol) was dissolved in dichloromethane (5 ml). To the solution, with ice cooling, were added a mixture of acetic anhydride (0.102 g, 1 mmol) and formic acid (0.046 g, 1 mmol) which had been heated at 50° C. for 30 minutes, and pyridine (0.08 g, 1 mmol), followed by stirring for 1 hour. After the addition of iced water (20 ml), the reaction liquid was extracted with dichloromethane (20 ml). The extract was washed with water, dried with anhydrous magnesium sulfate, and concentrated under reduced pressure. For isolation and purification, the concentrate was subjected to silica gel flush column chromatography (eluted with benzene: ethyl acetate=5:1). A quantity of 0.304 g (85%) of desired compound was obtained.

NMR δ ppm (CDCl$_3$): 3.71 (2H, s), 3.76 (3H, s), 3.82 (3H, s), 4.27 (1H, d, J=13 Hz), 4.42 (1H, d, J=13 Hz), 6.93 (1H, s), 7.1–7.6 (14H, m), 7.7–7.9 (2H, m), 8.27 (1H, s), 8.53 (1H, s).

What is claimed is:

1. A cephem compound represented by formula (III)

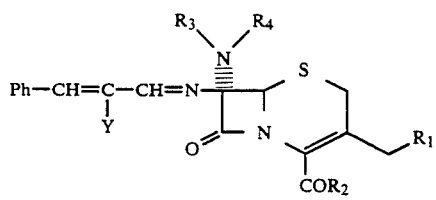

(III)

wherein $R_1$ denotes a hydrogen atom or a group-A-B (where A denotes an oxygen atom or sulfur atom and B denotes (a) an acyl group, (b) a group selected from the group consisting of 1H-tetrazol-5-yl, 1-methyl-1H-tetrazol-5-yl, 1-carboxymethyl-1H-tetrazol-5-yl, 2-carboxymethyl-1H-triazol-5-yl, 1-sulfoethyl-1H-tetrazol-5-yl, 2-carboxymethyl-1-methyl-1H-triazol-5-yl, 4-methyl-5-oxo-6-hydroxy-4,5-dihydro-1,2,4-triazin-3-yl, pyridiniummethyl, a triazolyl and a thiadiazolyl, or (c) a substituted or unsubstituted carbamoyl group; $R_2$ denotes a protective group for the hydroxyl group or carboxyl group; $R_3$ and $R_4$ are the same or different, each representing a hydrogen atom or a lower alkyl group having 1 to 4 carbon atoms, or $R_3$ denotes a hydrogen atom and $R_4$ denotes a lower alkoxyl group having 1 to 4 carbon atoms; and Y denotes a chlorine atom or bromine atom.

2. A compound set forth in claim 1 which is 7β-(2-chloro(3-phenylprop-2-en-1-ylideneamino))-7α-amino-3-(1-methyl-1H-tetrazol-5-yl)thiomethyl-3-cephem-4-carboxylic diphenylmethyl ester.

3. A compound set forth in claim 1 which is 7β-(2-chloro(3-phenylprop-2-en-1-ylideneamino))-7α-amino-3-(2-methyl-1,3,4-thiadiazol-5-yl)thiomethyl-3-cephem-4-carboxylic diphenylmethyl ester.

4. A compound set forth in claim 1 which is 7β-(2chloro-(3-phenylprop-2-en-1-ylideneamino))-7α-methoxyamino-3-(1-methyl-1H-tetrazol-5-yl)thiomethyl-3-cephem-4-carboxylic diphenylmethyl ester.

5. A compound set forth in claim 1 which is 7β-(2-chloro(3-phenylprop-2-en-1-ylideneamino))-7α-methylamino-3-(1-methyl-1H-tetrazol-5-yl)thiomethyl-3-cephem-4-carboxylic diphenylmethyl ester.

6. A compound set forth in claim 1 which is 7β-(2-chloro(3-phenylprop-2-en-1-ylideneamino))-7α-dimethylamino-3-(1-methyl-1H-tetrazol-5-yl)thiomethyl-3-cephem-4-carboxylic diphenylmethyl ester.

* * * * *